(12) United States Patent
Liang

(10) Patent No.: US 7,113,651 B2
(45) Date of Patent: Sep. 26, 2006

(54) MULTI-SPECTRAL MINIATURE MICROSCOPE ARRAY

(75) Inventor: Chen Liang, Tucson, AZ (US)

(73) Assignee: DMetrix, Inc., Tucson, AZ (US)

( * ) Notice: Subject to any disclaimer, the term of this patent is extended or adjusted under 35 U.S.C. 154(b) by 791 days.

(21) Appl. No.: 10/300,679

(22) Filed: Nov. 20, 2002

(65) Prior Publication Data

US 2004/0096118 A1    May 20, 2004

(51) Int. Cl.
*G06T 5/50* (2006.01)
*G02B 27/10* (2006.01)

(52) U.S. Cl. ................................ 382/284; 359/619

(58) Field of Classification Search ............... 382/284; 359/619, 198, 368, 373; 250/208.1
See application file for complete search history.

(56) References Cited

U.S. PATENT DOCUMENTS

| | | | | |
|---|---|---|---|---|
| 4,190,330 | A | 2/1980 | Berreman | 350/331 |
| 4,270,838 | A | 6/1981 | Furusawa et al. | 350/81 |
| 4,301,252 | A | 11/1981 | Baker et al. | 435/290 |
| 4,911,782 | A | 3/1990 | Brown | 156/633 |
| 4,974,094 | A | 11/1990 | Morito | 358/225 |
| 5,200,152 | A | 4/1993 | Brown | 422/102 |
| 5,260,826 | A | 11/1993 | Wu | 359/363 |
| 5,499,112 | A | 3/1996 | Kawai et al. | 358/475 |
| 5,503,803 | A | 4/1996 | Brown | 422/102 |
| 5,742,419 | A | 4/1998 | Dickensheets et al. | 359/201 |
| 5,748,371 | A | 5/1998 | Cathey, Jr. et al. | 359/558 |
| 5,861,113 | A | 1/1999 | Choquette et al. | 264/1.24 |
| 5,871,558 | A | 2/1999 | Takei et al. | 65/17.21 |
| 5,907,425 | A | 5/1999 | Dickensheets et al. | 359/224 |
| 5,976,425 | A | 11/1999 | Nomura et al. | 264/2.2 |
| 6,007,208 | A | 12/1999 | Dickensheets et al. | 359/872 |
| 6,023,495 | A | 2/2000 | Adler et al. | 378/4 |
| 6,027,208 | A | 2/2000 | Amano | 347/70 |
| 6,040,943 | A | 3/2000 | Schaub | 359/565 |
| 6,064,529 | A | 5/2000 | McDonald et al. | 359/637 |
| 6,069,738 | A | 5/2000 | Cathey, Jr. et al. | 359/558 |
| 6,088,145 | A | 7/2000 | Dickensheets et al. | 359/196 |
| 6,094,411 | A | 7/2000 | Matsuda | 369/102 |
| 6,097,485 | A | 8/2000 | Lievan | 356/338 |
| 6,101,028 | A | 8/2000 | Heacock et al. | 359/368 |
| 6,105,395 | A | 8/2000 | Yoshida et al. | 65/102 |
| 6,133,986 | A | 10/2000 | Johnson | 355/67 |
| 6,150,653 | A | 11/2000 | Assadi et al. | 250/216 |
| 6,154,305 | A | 11/2000 | Dickensheets et al. | 359/225 |
| 6,175,655 | B1 | 1/2001 | George, III et al. | 382/257 |
| 6,177,980 | B1 | 1/2001 | Johnson | 355/67 |
| 6,191,881 | B1 | 2/2001 | Tajima | 359/254 |

(Continued)

FOREIGN PATENT DOCUMENTS

CN        1104770        7/1995

(Continued)

OTHER PUBLICATIONS

J. R. Benford, Microscope Objectives, Ch. 4 in Applied Optics and Optical Engineering, vol. 333, ed. R. Kingslake (Academic Press, 1965).

(Continued)

*Primary Examiner*—Sanjiv Shah
(74) *Attorney, Agent, or Firm*—Birdwell & Janke, LLP

(57) ABSTRACT

A multi-spectral miniature microscope objective imaging system for a miniature microscope array includes one or more illuminating light sources for illuminating an object with light including multiple spectral bands, a multi-spectral imaging miniature microscope objective for imaging the object, and one or more detectors for detecting a images corresponding to each of the multiple bands separated from other wavelengths of the light.

25 Claims, 8 Drawing Sheets

U.S. PATENT DOCUMENTS

| | | |
|---|---|---|
| 6,201,899 B1 | 3/2001 | Bergen ................ 382/284 |
| 6,260,997 B1 | 7/2001 | Claybourn et al. ........ 374/45 |
| 6,320,174 B1 | 11/2001 | Tafas ................ 250/208.1 |
| 6,327,102 B1 | 12/2001 | Naulleau et al. ........ 359/802 |
| 6,341,180 B1 | 1/2002 | Pettersson et al. ........ 382/255 |
| 2001/0006783 A1 | 7/2001 | Nogami ................ 435/6 |
| 2003/0067680 A1 | 4/2003 | Weinstein ................ 359/372 |
| 2003/0103262 A1 | 6/2003 | Descour et al. |
| 2003/0108347 A1 | 6/2003 | Manico ................ 396/207 |
| 2003/0123155 A1 | 7/2003 | Quake ................ 359/664 |
| 2004/0004759 A1* | 1/2004 | Olszak ................ 359/373 |
| 2004/0051030 A1* | 3/2004 | Olszak et al. ........ 250/208.1 |
| 2004/0051940 A1* | 3/2004 | Liang et al. ............ 359/368 |
| 2004/0056177 A1* | 3/2004 | Olszak et al. ........ 250/208.1 |
| 2004/0057094 A1* | 3/2004 | Olszak et al. ............ 359/198 |
| 2004/0057120 A1* | 3/2004 | Olszak et al. ............ 359/619 |
| 2004/0101210 A1* | 5/2004 | Weinstein et al. ........ 382/284 |
| 2004/0223226 A1* | 11/2004 | Liang et al. ............ 359/619 |

FOREIGN PATENT DOCUMENTS

| | | |
|---|---|---|
| CN | 1335527 | 2/2002 |
| DE | 31 38 587 A1 | 5/1982 |
| DE | 37 01 013 A1 | 7/1988 |
| DE | 197 44 246 A 1 | 4/1999 |
| DE | 199 06 960 A1 | 8/2000 |
| EP | 0 697 602 A2 | 2/1996 |
| EP | 0 751 533 A1 | 1/1997 |
| EP | 0 951 861 A1 | 10/1999 |
| GB | 2 062 276 A | 5/1981 |
| GB | 2 197 981 A | 6/1988 |
| GB | 2 340 332 A | 2/2000 |
| WO | WO 97/34171 | 9/1997 |
| WO | WO 99/04301 | 1/1999 |
| WO | WO 99/22226 | 5/1999 |
| WO | WO 00/20898 | 4/2000 |
| WO | WO 01/84130 A2 | 4/2001 |
| WO | WO 02/075370 A2 | 9/2002 |

OTHER PUBLICATIONS

D.S. Goodman, Basic Optical Instruments, Ch. 4 in Geometrical and Instrumental Optics, D. Malacara, ed. (Academic Press, 1988).

S.L. Webb, et al., Design of a 600-Pixel-per-Inch, 30-Bit Color Scanner, Hewlett-Packard Journal, Feb. 1997, Article 8, p. 1-10.

J.M. Sasian, et al., Design Approaches with a Lenslet Array and a Single, High-Numberical-Aperture Annular-Field Objective Lens for Optical Data Storage Systems that Incorporate Large Numbers of Parallel Read-Write-Erase Channels, Applied Optics, (Mar. 1, 1999), vol. 38, No. 7, pp. 1163-1168.

M.R. Descour, et al., A Ring-Toric Lens for. Focus-Error Sensing in Optical Data Storage, Applied Optics, (Mar. 10, 1999), vol. 38, No. 8, pp. 1388-1392.

J.T. Rantala, et al., Direct UV Patterning of Thick Hybrid Glass Films for Micro-Opto-Mechanical Structures,(Mar. 16, 2000), Electronics Letters, vol. 36, No. 6, pp. 530-531.

NSF Award Abstract—#0124922, AWSFL008-DS3, start date: Aug. 1, 2001.

M.R. Descour, et al., Toward the Development of Miniaturized Imaging Systems for Detection of Pre-Cancer, IEEE Journal of Quantum Electronics, (Feb. 2002), vol. 38, No. 2, pp. 122-130.

C. Liang, et al., Design of a High-Numerical-Aperture Miniature Microscope Objective for an Endoscopic Fiber Confocal Reflectance Microscope, Applied Optics, (Aug. 1, 2002), vol. 41, No. 22, pp. 4603-4610.

C. Liang, Design of Miniature Microscope Objective Optics for Biomedical Imaging, U.S. Appl. No. 60/401,436, filed Aug. 6, 2002.

S. Yashvinder, et al., Slit-scanning confocal microendoscope for high-resolution *in vivo* imaging, Applied Optics, Dec. 1, 1999, pp. 7133-7144, vol. 38, No. 34.

J. Knittel, et al., Endoscope-compatible confocal microscope using a gradient index-lens system, Optics Communications, Feb. 15, 2001, pp. 267-273, No. 188.

* cited by examiner

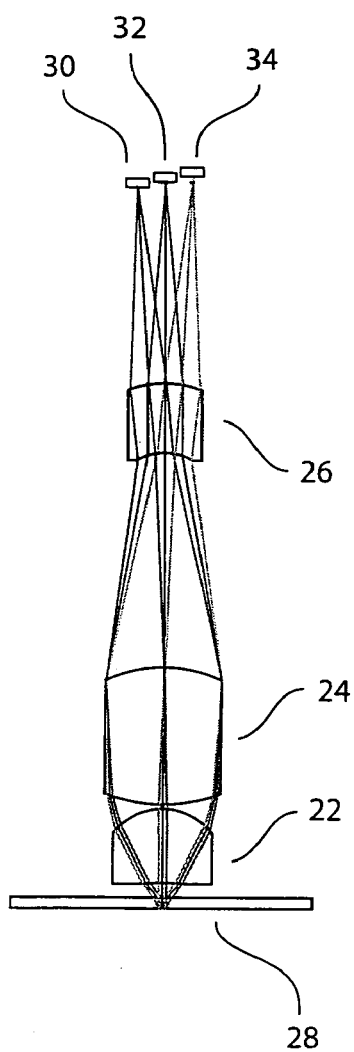
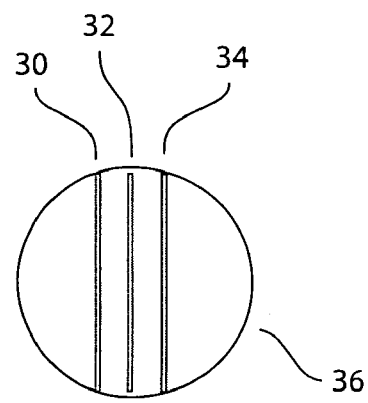
Figure 2b
Figure 2a

MULTI-SPECTRAL MINIATURE MICROSCOPE ARRAY

BACKGROUND

1. Field of the Invention

The invention relates to miniature microscope objectives, and particularly to miniature objective arrays for multi-spectral imaging.

2. Discussion of the Related Art

Miniaturization of microscope objective optics, e.g., to less than a few mm or less than around 5 mm in diameter, has many potential applications in imaging. It is the enabling technology for the construction of a microscope array such as the miniature microscope array (MMA). Moreover, miniature microscope objective designs for MMA have certain characteristics that are uncommon from typical microscope objectives.

Imaging in multiple spectral bands is extremely useful in microscopy applications. For example, to construct a color image of an object for visual inspection, it is desired to image the object at multiple wavelength bands, and preferably at three spectral bands corresponding to red, green, and blue. For non-visual inspection, it may be advantageous to image the object at different or additional wavelengths even including non-visible wavelengths, and perhaps at more than three spectral bands determined by the object's material properties.

A MMA includes many miniature microscope objectives. Each one of MMA's individual microscope objective forms a 2D image. MMA preferably is used as a scanning system, and so a thin, substantially linear portion of an entire 2D image is used as an object is scanned. In this case, the rest of the image is not used.

It is recognized in the present invention that one can take advantage of this situation by scanning the object at different spectral bands simultaneously or substantially simultaneously. For example, multiple linear detectors equipped with different spectral filters may be used to simultaneously image an object at multiple spectral bands. The number of spectral bands imaged may depend on the size of the 2D images and the area of the available image field, i.e., how many linear detectors can fit in that image field.

SUMMARY OF THE INVENTION

In view of the above, a multi-spectral miniature microscope objective imaging system, a multi-spectral imaging miniature microscope objective for imaging the object at multiple spectral bands, and one or more and preferably multiple detectors for detecting images corresponding to each of the multiple bands separated from other wavelengths of the light. Preferably, the multiple bands are detected simultaneously. The miniature objective is preferably part of a miniature microscope array including multiple such objectives.

The multiple bands can be detected within a same image plane, or alternatively, the multiple bands can be detected at different image planes. The multiple bands may be preferably detected within the same image plane when the objective is substantially chromatically corrected. If the objective is not substantially chromatically corrected, then one or more plates for accommodating the different optical path lengths of the spectral bands may be inserted so that the multiple bands may be detected in the same image plane. Also, for an objective that is not substantially chromatically corrected, different spectral bands may be detected in different image planes. In a preferred embodiment, the multiple bands are detected within a same image field.

The system preferably further includes one or more illuminating light sources for illuminating the object with light including the multiple bands. The light sources may include trans-illuminating and/or epi-illuminating light sources, and may be broadband or generate discrete spectral bands of light. A reflector may reflect the illuminating light towards the object for epi-illumination of the object to be imaged. The light may also be transmitted towards the object from the direction opposite of the imaging optics for trans-illumination of the object to be imaged. The light preferably includes first, second and third bands, e.g., red, green and blue, respectively. Ambient light may alternatively also be used to provide broadband illumination.

Preferably, multiple detectors detect multiple images corresponding to the multiple bands separated from other wavelengths of the light including the other band or bands. Different detectors may have pixels of different sizes corresponding to different image sizes or magnifications of different bands.

When multiple detectors are used, they may be disposed at same axial positions. The objective may be substantially corrected for axial chromatic aberrations such that first and second spectral bands are detected in a substantially same image plane, or alternatively, a block of material, e.g., having plane-parallel surfaces with anti-reflection coatings, in the optical path between the object and a detector may be used to adjust the geometrical path length of a band to be substantially the same as that of another band, even though their optical path lengths may differ. The detectors may also be disposed at different axial positions corresponding to different axial path lengths.

One or more spectral filters or other optics before the one or more detectors may filter light outside a particular band from detected images. A dichroic optic may separate a first band from the rest of the light that may include a second band also to be detected.

Images detected by the one or more detectors corresponding to different bands can be preferably combined into a multi-spectral image. A processor or other electronics may be used to combine data corresponding to the images. The processor may digitally rescale an image corresponding to a band to a substantially same size as another image corresponding to a different band before combining the images.

A method is provided for multi-spectral imaging with a multi-spectral imaging miniature microscope objective that is not substantially chromatically corrected. The method includes imaging the object with the multi-spectral imaging miniature microscope objective without substantial chromatic correcting, separating a first spectral band from at least a first portion of light, detecting the first band, and detecting a second spectral band. The first and second bands are preferably simultaneously detected. The first and second bands are also preferably detected in a same image field.

A further method is provided for multi-spectral imaging with a multi-spectral imaging substantially chromatically corrected miniature microscope objective of a miniature microscope array (MMA) including multiple such objectives. The method includes imaging the object with the multi-spectral imaging miniature microscope objective including substantial chromatic correcting, separating a first spectral band from at least a first portion of light, detecting the first band, and detecting a second spectral band. The first and second bands are preferably simultaneously detected. The first and second bands are also preferably detected in a same image field.

BRIEF DESCRIPTION OF THE DRAWINGS

FIG. 2a schematically illustrates an imaging system including a multi-spectral miniature microscope objective according to a second embodiment. Images of three spectral bands are shown in this figure and their axial positions are displaced. This miniature microscope objective can be part of a miniature microscope array.

FIG. 2b illustrates a top view of three linear detectors of the system of FIG. 2a. The three linear detectors can be used to image three different spectral bands.

INCORPORATION BY REFERENCE

Figure 1A:
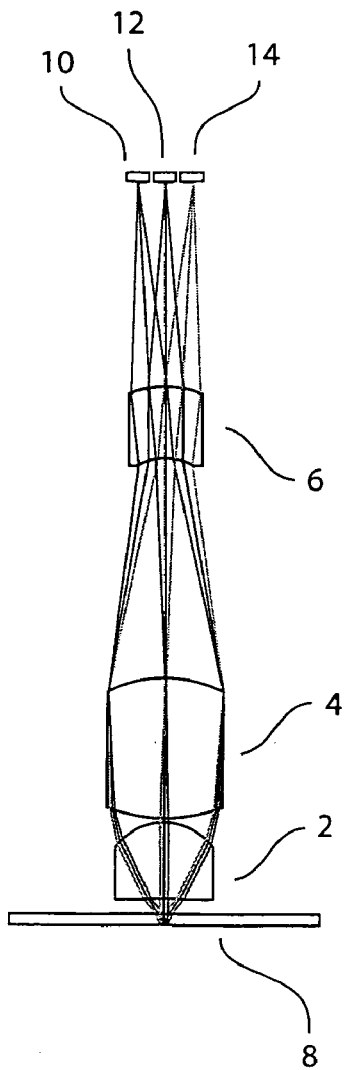
FIG. 1a schematically illustrates an imaging system including a multi-spectral miniature microscope objective according to a first embodiment. Three spectral bands are shown in this figure. This miniature microscope objective can be part of a miniature microscope array.

What follows is a cite list of references each of which is, in addition to that which is described in the Background, Invention Summary and Drawings Description, and those references cited above in the priority section, hereby incorporated by reference into the Detailed Description of the Preferred Embodiments below, as disclosing alternative embodiments of elements or features of the preferred embodiments not otherwise set forth in detail below. A single one or a combination of two or more of these references may be consulted to obtain a variation of the preferred embodiments described in the detailed description below. Further patent, patent application and/or non-patent references are cited in the written description and are also incorporated by reference into the preferred embodiment with the same effect as just described with respect to the following references:

Steven L. Webb, Kevin J. Youngers, Michael J. Steinle, and Joe A. Eccher, "Design of a 600-pixel-per-inch, 30-Bit Color Scanner," Hewlett-Packard Journal, February 1997;

U.S. Pat. Nos. 6,064,529, 6,040,943, 6,023,495, 6,175,655, 5,871,558, 6,150,653, 5,861,113, 6,105,395, 5,976,425, 6,341,180, 6,191,881, 4,190,330, 5,748,371, 6,069,738, 6,201,899, 6,177,980, 6,133,986, 6,154,305, 6,088,145, 6,067,208, 5,742,419 and 5,499,112;

PCT published applications No. WO 97/34171 and PCT/US02/08286;

U.S. patent applications Ser. Nos. 60/318,059, 60/276,498, 60/401,436, 10/247,811, 10/158,626, and serial number not known to Descour et al., entitled, "Multimodal Miniature Microscope, filed Sep. 6, 2002;

Descour et al., Toward the Development of Miniaturized Imaging Systems for Detection of Pre-Cancer, IEEE Journal of Quantum Electronics, Vol. 38, No. 2 (February 2002);

Liang et al., Design of a high-numerical aperture miniature microscope objective for an endoscopic fiber confocal reflectance microscope, Applied Optics, Vol. 41, No. 22 (Aug. 1, 2002);

Geometrical and Instrumental Optics, Vol. 25, Methods of Experimental Physics, Daniel Malacara, ed., see particularly pp. 67–99 and 158–173, (Academic Press, 1988);

J. M. Sasian, et al., Applied Optics 38, pp. 1163–1168 (1999);

G. H. Rieke, Detection of Light: From the Ultraviolet to the Submillimeter, Ch. 7 (Cambridge University Press, 1994);

R. G. Driggers, et al., Introduction to Infrared and Electro-Optical Systems, Ch. 8 (Artech House, 1999);

Wyrowski and Turner, Diffractive Optics for Industrial and Commercial Applications, John Wiley and Sons;

H. K. Schmidt, Sol-gel and polymer photonic devices, SPIE Critical Review, Vol. CR68, pp. 192–203 (1995);

Rantala et al., Direct patterning of thick hybrid glass film for micro-opto-mechanical structures, Electronics Letters, Vol. 36, pp. 1–2 (2000);

J. R. Benford, Microscope Objectives, Ch. 4 in Applied Optics and Optical Engineering, Vol. III, ed. R. Kingslake (Academic Press, 1965);

D. Malacara, Optical Shop Testing, $2^{nd}$ edition (Wiley, 1992);

M. Mansuripur, The Principles of Magneto-Optical Recording, Ch. 8, Section 3, pp. 264–277 (Cambridge University Press, 1995); and R. R. Shannon, The Art and Science of Optical Design, (Cambridge University Press, 1997);

G. M. Morris and K. J. McIntyre, "Optical system design with diffractive optics," in Diffractive Optics for Industrial and Commercial Applications, J. Turunen and F. Wyrowski, eds., Ch. 3 (Akademie Verlag, 1997);

D. S. Goodman, "Basic Optical Instruments," Ch. 4 in Geometrical and Instrumental Optics, D. Malacara, ed. (Academic Press, 1988); and M. R. Descour, et al., A ring-toric lens for focus-error sensing in optical data storage, Applied Optics, Vol. 38, No. 8, pp. 1388–1392 (Mar. 10, 1999).

DETAILED DESCRIPTION OF THE PREFERRED EMBODIMENTS

FIG. 1a schematically illustrates an imaging system including a multi-spectral miniature microscope objective according to a first embodiment. The objective includes three lens elements 2, 4, 6 for imaging an object located at an object plane 8. The objective of FIG. 1a may be one or several objectives forming a miniature microscope array (MMA). Preferred embodiments of the miniature microscope array are set forth in detail at PCT/US02/08286, entitled "Mimiature Microscope Array Digital Slide Scanner", and some details are provided below with reference to FIGS. 5–7.

The objective preferably includes three or four lenses, and perhaps two lenses. The three lens design is preferably a positive, positive, negative or PPN design, and the four lens design may be preferably PPNP, PPPN or PPNN. The three or four lens objective preferably has a numerical aperture (NA) between 0.4 and 0.9 and a magnification (M) of 12 or less and preferably more than M=4, and the two lens design has NA preferably close to 4. The ratio of M to NA is preferably less than the outer diameter (OD) of the optics divided by the product of field of view (FOV) and NA. That is, M/NA is preferably below 30 and FOV/OD is preferably more than 0.1, where FOV is preferably between 220–240 microns or more and OD is preferably 1.6 to 2.0 mm or less. An aperture stop may be located on the front or back surface, or within, the second positive lens. A diffractive surface may be included such that the objective may be corrected over an enhanced bandwidth. The lenses may comprise such materials as COC, Zeonex™, polystyrene and/or LAK-10, and one or more gradient index lenses may be used. Exemplary optical prescriptions for three and four lens objective designs are provided below at Tables 1 and 2. Further details of preferred objectives of the multi-spectral miniature microscope are set forth at U.S. patent application Ser. No. 10/247,781, which is assigned to the same assignee as the present application and is hereby incorporated by reference, and/or others of the patent applications incorporated by referernce above.

The system schematically illustrated at FIG. 1*a* also includes three detectors 10, 12, and 14. An alternative system may include only two detectors or more than three. A single detector may be used, wherein certain pixels are used to detect one image and certain other pixels are used to detect at least one other image. In this sense, even if one physical detector is used, wherein different regions of pixels on that detector are used to separately detect different images, then this arrangement is deemed in the present application to include the use of "multiple detectors". Each detector 10, 12, and 14, or each set of pixels used to detect a particular image, is used to detect an image corresponding to a certain spectral band. For example, detector 10 may detect a red image, detector 12 may detect a blue image, and detector 14 may detect a green image. Bands including wavelengths outside the visible region, such as in the infrared, and ultraviolet (near, far, deep, vacuum, extreme, . . . ), may also be detected with proper optics.

If the objective is well corrected for chromatic aberrations, then images corresponding to different spectral bands will substantially coincide at a same axial location with a same magnification. If this is the case, then multiple linear detectors 10, 12, 14 may be disposed within a single image plane, as shown in FIG. 1*a*. The optical path lengths for the different bands are the same, and the geometrical path lengths are also the same, in this embodiment including a substantially chromatically corrected objective.

Each optical path preferably includes means for filtering other wavelengths, so that only the band of wavelengths desired to be detected for that image reach the pixels of the detector 10, 12 or 14. That is, each detector 10, 12, 14 is used to for detecting an image corresponding to a particular spectral band. One or more spectral filters may be used to eliminate unwanted wavelengths by absorption or interference. The filter can also be in the form of dichroic filter that transmits desired wavelength while reflecting unwanted wavelengths. The reflected light may be dumped or one or more bands within the reflected light may be detected by another detector as an additional image. The light may be filtered more than once before it is detected.

Figure 1B:
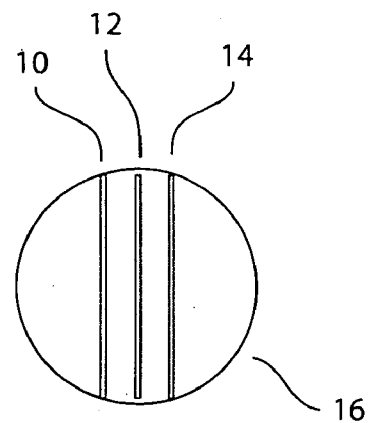
FIG. 1b illustrates a top view of three linear detectors of the system of FIG. 1a. The three linear detectors can be used to image three different spectral bands.

FIG. 1*b* illustrates a top view of three linear detectors 10, 12 and 14 of the system of FIG. 1*a*. The 2D image field is indicated as reference numeral 16. Note that the detectors 10, 12, 14 are substantially linear, and are substantially relatively parallel oriented. The long direction of each of the linear detectors 10, 12, 14 is oriented perpendicular to the direction of the scan. Preferably the images at each detector 10, 12, 14 do not overlap, such as in FIG. 1*b*. In the arrangement of FIG. 1*b*, the images may advantageously be detected at detectors 10, 12 and 14 simultaneously. Moreover, each detected image at detectors 10, 12 and 14 may advantageously be detected within the same image field of the objective.

Discrepancies in the signal strength, gain and offset for each linear detector can be corrected digitally or with analog electronics when comparing or combining the images. The images captured by different linear detectors can be used separately or they can be combined together.

One or more illuminating light sources may be used. A single broadband source may be used. Two or more sources emitting particular bands of light may be used, e.g., red, green and blue sources may be used to illuminate the object, with red, green and blue images being detected. When ambient light is contemplated to be sufficient, then an alternative embodiment would include no illuminating light source. Trans-illumination or epi-illumination (see FIG. 4*a* and description below), or a combination of these, may be used. The light may be transmitted through, reflected from or scattered by the object 8 to the detectors 10, 12, 14.

If a broad band source is used, then the object can be illuminated in its entirety; or sections of the object that are conjugate to the detectors can be illuminated. For example, if three linear detectors are used then just the three stripes on the object may be illuminated. Spectral filters are preferably used for each linear detector. If multiple narrow band sources are used, then the object is preferably illuminated only at sections that are conjugate to the detectors. Alternatively the sources can be pulsed and different sources can be turned on sequentially.

Referring now to the second embodiment schematically illustrated at FIG. 2*a*, the imaging system shown includes an objective of three lenses 22, 24, 26, and may alternatively include two or four or more, and three detectors 30, 32, 34 for detecting images of the object 28. Other system details may be as described above with reference to FIG. 1*a*, or at the U.S. patent application Ser. No. 10/247,781 application, or otherwise as understood by those skilled in the art. The objective of this second embodiment is alternatively designed compared with the first embodiment, in that it is not well corrected for chromatic aberrations, and as such has a simpler design that may be advantageous under certain circumstances. In this case, the images formed at the detectors 10, 12, 14 corresponding to the different spectral bands will be located at different axial locations due to axial chromatic aberration. Additionally, the magnification of different spectral images will be different due to lateral chromatic aberration.

Advantageously, the detectors 30, 32, 34 are staggered or relatively axially displaced. That is, to compensate for the axial chromatic aberration, each linear detector 30, 32, 34 for detecting an image corresponding to a specific spectral band, e.g., as determined by a spectral filter before the detector, is positioned at a different axial position, or at least the constraint of having the detectors 30, 32, 34 all in the same image plane is relaxed and the axial positioning of each of the detectors 30, 32, 34 is independently determined. The axial displacement of different spectral band images can be readily calculated using lens design software such as ZEMAX, and then preferably, the detectors 30, 32, 34 are mounted at fixed axial positions corresponding to best image planes for their particular spectral bands. Alternatively, one or more of the detectors 30, 32, 34 may be mounted to axially adjustable mounts for adjusting the axial position on-line, and there may even be a feedback mechanism for performing the adjustments using a processor (not shown).

If different spectral images are used separately, then the lateral chromatic aberration may not be a concern. If the different spectral images are going to be combined together into a multi-spectral image, e.g., as in the case of forming a RGB image, then the lateral chromatic aberration is preferably also addressed in the second embodiment. Lateral chromatic aberration causes images of different spectral bands to have different magnifications and therefore different sizes. In a first embodiment, one or more of the detected images is digitally rescaled and/or re-sampled to a same size as one of the other images or to a selected scale. In a second embodiment, different linear detectors are used for different spectral bands. For example, for spectral bands corresponding to larger magnifications, linear detectors having correspondingly larger pixel sizes are used.

FIG. 2b illustrates a top view of three linear detectors 30, 32, 34 of the system of FIG. 2a within a 2D image plane 36. Although FIG. 2b looks the same as FIG. 1b, it is interesting that these same linear detectors 30, 32, 34 as detectors 10, 12, 14 from their respective top views may be relatively axially displaced in the second embodiment and be in the same axial plane in the first embodiment, and the objective of the first embodiment is chromatically corrected, while the objective of the second embodiment is not.

Figure 3A:
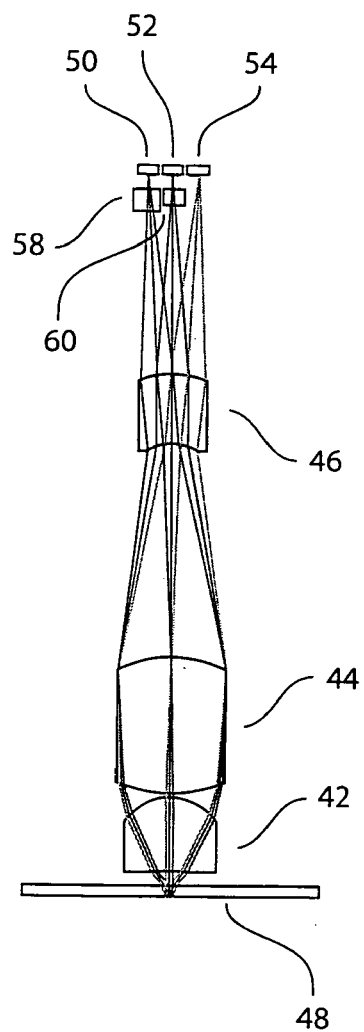
FIG. 3a schematically illustrates an imaging system including a multi-spectral miniature microscope objective and plane parallel plates for adjusting geometrical path lengths according to a third embodiment; the fourth embodiment of FIG. 3b has the plates alternatively disposed in object space. This miniature microscope objective can be part of a miniature microscope array.

FIG. 3a schematically illustrates an imaging system according to a third embodiment including a multi-spectral miniature microscope objective with lenses 42, 44, 46 and detectors 50, 52, 54 for imaging an object 48 in a scanning process. The objective lenses 42, 44, 46 are substantially the same as those of the second embodiment and FIG. 2b, and the detectors 50, 52, 54 are substantially the same as those described above with reference to the first embodiment and FIG. 1a. That is, the objective of this third embodiment is not chromatically corrected, and the detectors 50, 52, 54 are disposed in a same axial plane.

Optical path length correction for different spectral bands is advantageously achieved using one or more plane parallel plates 58, 60 for adjusting optical path lengths corresponding to one or more of the spectral bands. For example, the detector 54 may be placed at an optimal axial location to detect a blue image. This same plane is not optimal for detector 52 and detector 50 to detect a green image and a red image, respectively, due to their optical path lengths being different than that of the blue image. The optimal image planes for the red and green images also differ.

Advantageously, the plate 58 has an index of refraction and thickness selected to make the geometrical path length for the red image the same as that of the blue image, and the plate 60 has an index of refraction and thickness selected to make the geometrical path length for the green image the same as that of the blue and red images. The plate 58 may have a different thickness than plate 60, or may have a different index of refraction, or both. A third plate (not shown) may be used for adjusting the path length of the blue image, such that none of the detectors are at their optimal axial positions and are instead in a plane selected for another reason such as a desired length of the system, a convenient detector fixation plane, etc.

The plates 58, 60 are preferably coated with anti-reflection coatings to reduce stray reflection and thus improve image contrast. It may be advantageous to slightly tilt one or more of the plates 58, 60, so that stray reflection from the detectors 50, 52 will not reflect off the plates 58, 60 and come back into the detectors 50, 52. The alignment accuracy of the plates 58, 60 does not need to be very high. The exact positions of the plates 58, 60 may vary as long as its geometrical path length adjustment is accurate and the entire image, e.g, the red image and the green image passes through its corresponding plate 50, 52.

Thus, an alternative to physically displacing the linear detectors 50, 52, 54 when the objective is not chromatically corrected is to displace them "optically" while geometrically locating them in a same plane. This is achieved in this third embodiment by inserting plane parallel plates 58 and 60 of appropriate thicknesses and/or refractive indices in front of linear detectors 50 and 52, respectively. Light traveling inside the plates 58, 60 experience different optical path lengths per unit geometric length compared to traveling in air, due to the larger refractive index within the material. By introducing plates 58, 60 of different thickness and/or refractive index to light of different spectral bands, the images of all spectral bands are formed at the same location and therefore compensates the axial chromatic aberration.

Figure 3C:
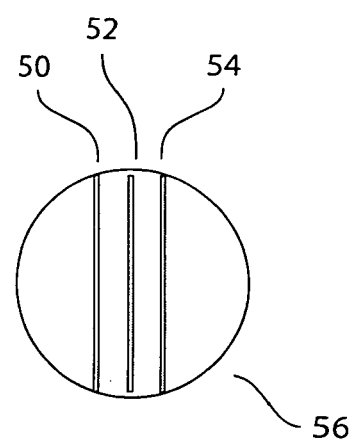
FIG. 3c illustrates a top view of three linear detectors of the system of either of FIGS. 3a and 3b. The three linear detectors can be used to image three different spectral bands.
Figure 3B:
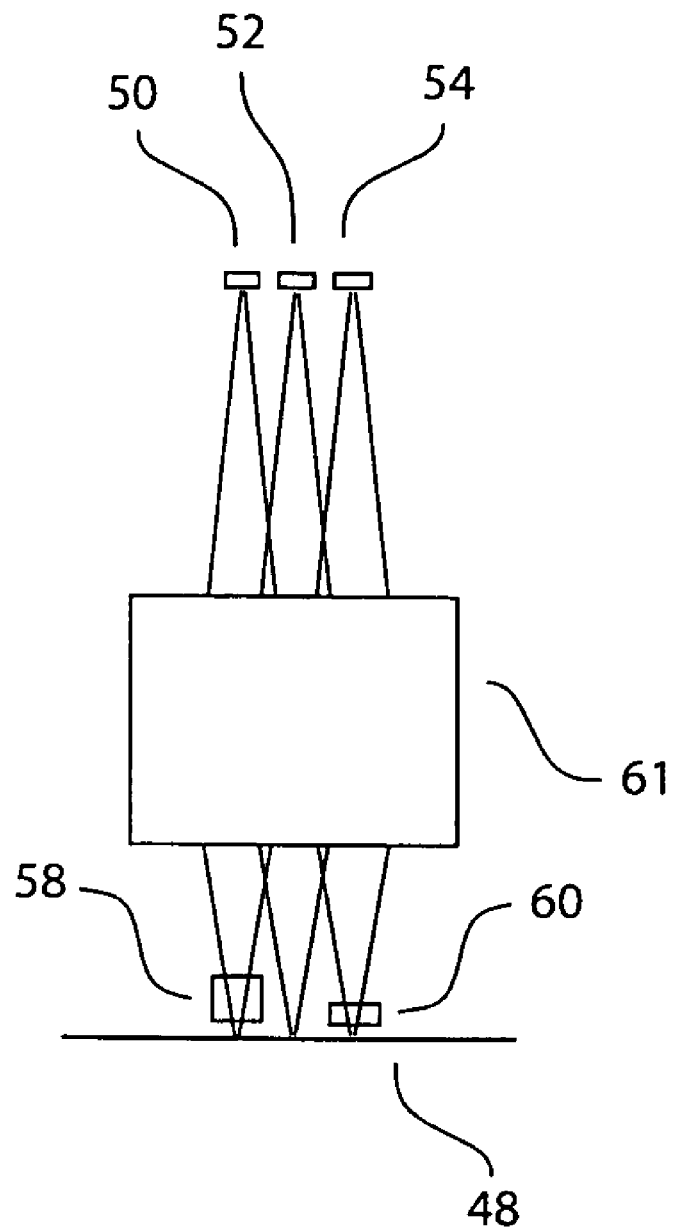
FIG. 3b schematically illustrates an imaging system an arbitrary optical system with relatively long working distance in object space and plane parallel plates for adjusting geometrical path lengths according to a fourth embodiment. This miniature microscope objective can be part of a miniature microscope array.

A fourth embodiment is illustrated at FIG. 3b. FIG. 3b schematically illustrates an imaging system including an arbitrary optical system 61 with relatively long working distance in object space and one or more plane parallel plates 58, 60 for adjusting geometrical path lengths according to a fourth embodiment. An object 48 is imaged by the optical system 61 of FIG. 3b. The system includes the detectors 50, 52, 54 on the image side of the optics 61 and the plates 58, 60 on the object side of the optics 61.

The fourth embodiment of FIG. 3b has the plates 58, 60 disposed in object space, alternatively from those disposed in image space of FIG. 3a. That is, the plates 58, 60 used in the fourth embodiment are switched to object space instead of image space as in the third embodiment. This fourth embodiment may be preferably used with an objective design 61 that has a long working distance. For the third and fourth embodiments, the lateral chromatic aberration can be compensated using the same method(s) as described with reference to the second embodiment.

FIG. 3c illustrates a top view of three linear detectors 50, 52, 54 of the system of FIG. 3a within a 2D image plane 56. Although FIG. 3b looks the same as FIGS. 1b and 2b, it is interesting that these same linear detectors 50, 52, 54 as detectors 10, 12, 14 and 30, 32, 34 from their respective top views may be relatively axially displaced in the second embodiment and be in the same axial plane in the first and third embodiments, while the objective of the first embodiment is chromatically corrected and the objectives of the second and third embodiments are not.

This third and fourth embodiments have several advantages. First, the multiple linear detectors 50, 52, 54 are co-planar. This allows the multiple linear detectors 50, 52, 54 to be fabricated together and share common electronics. The multiple detectors 50, 52, 54 may in fact be one array detector having different pixels used for each of the red, green and blue images. Second, less mechanical structure is needed to mount and support the image sensors 50, 52, 54, which will likely result in more space being freed up, such that, e.g., a larger number of linear detectors can be used to detect images corresponding to more spectral bands.

Figure 4:
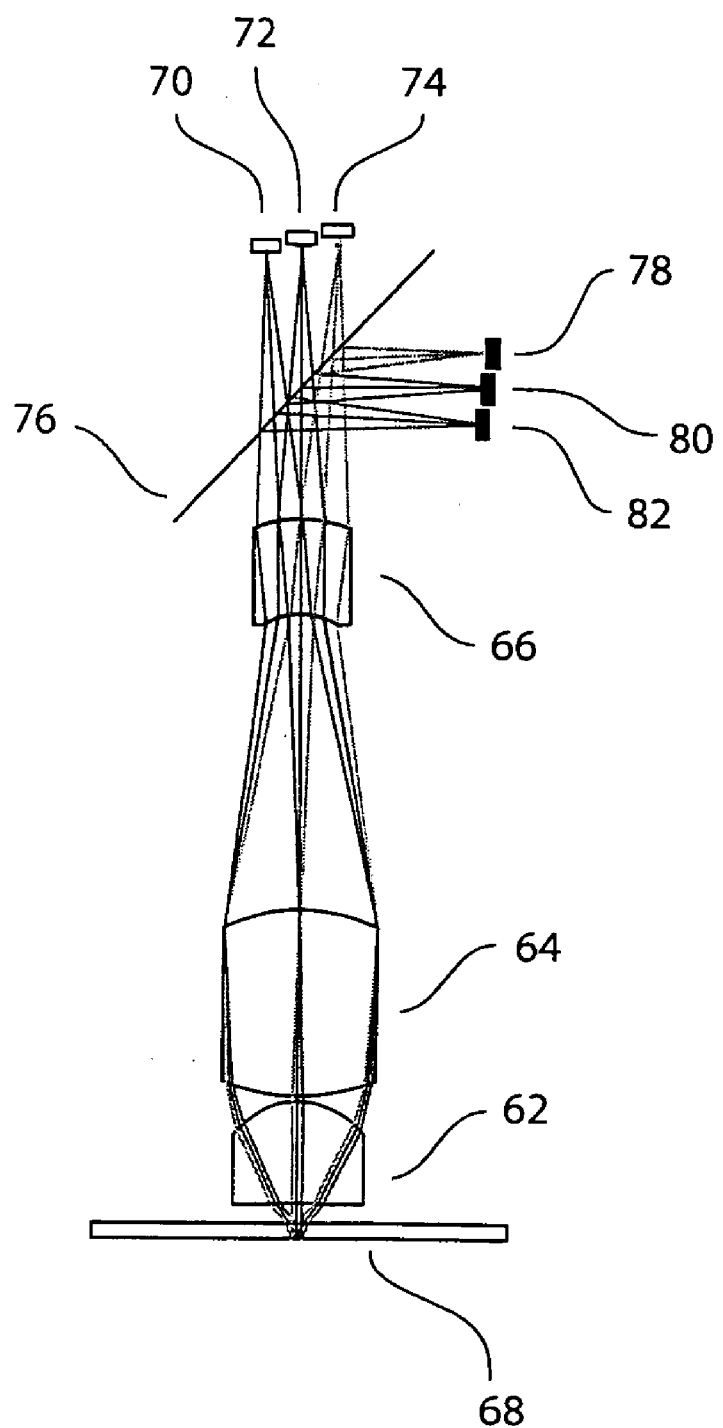
FIG. 4 schematically illustrates an imaging system including a multi-spectral miniature microscope objective according to a fifth embodiment. Epi-illumination is used for this embodiment. This miniature microscope objective can be part of a miniature microscope array.

Preferably, the first, second, third and fourth embodiments are configured for trans-illumination. However, any of them may be alternatively configured for epi-illumination, and as noted, under some circumstances, ambient light may be used. Epi-illumination may be implemented in several different ways. FIG. 4 schematically illustrates an imaging system as in any of the above embodiments, and particularly the second embodiment, including a multi-spectral miniature microscope objective with lenses 62, 64, 66 for imaging object 68 to axially relatively displaced detectors 70, 72, 74 for detecting images corresponding to different spectral bands. A beam splitter 76, such as a polarizing beam splitter or partially reflective mirror or dichroic beam splitter, reflects light from one or more an epi-illumiating light sources, in this case light sources 78, 80 and 82 generating three specific spectral bands such as red, green and blue. The light from the epi-illuminating light sources 78, 80, 82 is reflected by the beamsplitter 76 through the objective lenses 62, 64, 66, reflected or scattered from the object 68 back through the objective, transmitted through the beamsplitter 76 and imaged onto the detectors 70, 72, 74.

The beam splitter 76 is used to separate the illumination path and imaging path (see also, U.S. patent application Ser. No. 10/158,626, which is hereby incorporated by reference. Epi-illumination can also be achieved by using an integrated source and detector (see the '626 application. Epi-illumination can also be achieved by channeling the illumination light through the areas between the lenses 60, 62, 64 (see again the '626 application). Any one of the epi-illumination configurations described here can be implemented for simultaneously imaging multiple spectral bands within a same image field as in any of the first through fourth embodiments described above. Note that the fifth embodiment shown at FIG. 4a may be used in either reflectance mode or fluorescence mode.

The miniature microscope objective preferably includes at least three or four lenses, and may alternatively include only two lenses (see U.S. patent application Ser. No. 10/247, 811, assigned to the same assignee and incorporated by reference above). The three lens design preferably includes, from object to image, a first positive lens, a second positive lens and a third negative lens (PNN) according to, e.g., the optical prescription set forth at Table 1, below:

TABLE 1

PRESCRIPTION FOR FIG. 2, THREE LENS DESIGN

| Surf | Radius | Thickness | Glass | Diameter | Conic | 4th order | 6th order | 8th order |
|---|---|---|---|---|---|---|---|---|
| OBJ | Infinity | 0.150 | BK7 | 0.240 | 0 | | | |
| 1 | Infinity | 0.200 | | 0.390 | 0 | | | |
| 2 | −1.895 | 1.004 | COC | 0.668 | 0 | | | |
| 3 | −0.752 | 0.050 | | 1.397 | −0.226 | | | |
| 4 | 1.732 | 1.938 | COC | 1.607 | −2.568 | | | |
| STO | −1.646 | 2.437 | | 1.450 | 0 | 0.0232 | 0.0257 | −0.0087 |
| 6 | −0.669 | 1.000 | COC | 0.966 | 0 | | | |
| 7 | −1.507 | 2.414 | | 1.474 | 1.010 | | | |
| IMA | Infinity | | | 1.698 | 0 | | | |

The four lens design preferably includes at least one negative lens having a PPNP configuration, and alternatively a PPPN or PPNN configuration, according to, e.g., the optical prescription set forth at Table 2, below. A two lens design would preferably comprise and first positive lens and either a positive or a negative second lens.

TABLE 2

PRESCRIPTION FOR FIG. 4, FOUR LENS DESIGN

| Surf | Radius | Thickness | Glass | Diameter | Conic | 4th term | 6th term | 8th term |
|---|---|---|---|---|---|---|---|---|
| OBJ | Infinity | 0.15 | BK7 | 0.220 | 0 | | | |
| 1 | Infinity | 0.15 | | 0.397 | 0 | | | |
| 2 | Infinity | 1 | COC | 0.712 | 0 | | | |
| 3 | −0.61 | 0.05 | | 1.372 | −0.647 | | | |
| 4 | 2.08 | 1.2 | COC | 1.600 | −2.467 | | | |
| 5 | −1.43 | 0.05 | | 1.599 | −2.84 | | | |
| STO | −3.21 | 1.49 | POLYSTYR | 1.417 | 0 | 0.321 | −0.2 | 0.073 |
| 7 | 2.19 | 1.3 | | 1.234 | 6.86 | | | |
| 8 | 1.16 | 2.3 | COC | 1.600 | 0 | −0.155 | −0.038 | |
| 9 | 0.64 | 1.494649 | | 1.092 | −1.87 | | | |
| IMA | Infinity | | | 1.555 | 0 | | | |

The objective preferably exhibits certain numerical aperture and provides diffraction-limited performance. For example, the absolute value of the transverse magnification (M), hereinafter referred to simply as the "magnification", is below approximately an outer diameter (OD) divided by a field of view (FOV) of the objective. A ratio of M to NA is thus less than the outer diameter OD divided by the product of field of view (FOV) and numerical aperture (NA).

Preferably, the three or four lens objective design has a numerical aperture (NA) greater than NA=0.4, while the magnification (M) is preferably maintained at a magnitude of around M=11–12 or below, and also preferably greater than M=4. Thus, the ratio of M to NA for the objective has a magnitude greater than 1, and preferably greater than around 4.4, and less than substantially 27.5 to 30.

The field of view (FOV) for the three or four lens designs is preferably substantially 220–240 μm or more. The outer diameter (OD) is preferably substantially 1.6–2.0 mm or less, and the ratio of FOV to OD is thereby 0.11–0.15 or more.

In particularly preferred embodiments, NA is substantially 0.6–0.7 or more, and may be limited to being less than 0.9 for a four lens objective design, and to being less than around 0.8 for a three lens objective design. In this case, the ratio of M to NA may have a magnitude between 1.1 and 18.3, wherein particular ranges will vary depending on NA and M.

In further particularly preferred embodiments, M is substantially 7 or less, and NA may be between 0.4 and 0.9. In some embodiments, NA may be NA=0.6 or more, or NA=0.7 or more, or NA=0.9. In these cases, the M to NA ratio will be 17.5 or less, or may be 11.7 or less, or 10 or less or 7.8 or less. When M is 11–12 or less, the M to NA ratio for NA-0.6 or more, 0.7 or more, or 0.9, the M to NA ratio is, respectively, 20 or less, or 17.1 or less, or 13.3 or less.

An aperture stop may be located on the front or back surface of the second positive lens or within the lens. The first positive lens may be preferably plano-convex or a meniscus design, or alternatively bi-convex. The second positive lens may be preferably bi-convex or plano-convex, or alternatively meniscus. The preferred third negative lens may be a meniscus or a biconcave design, or alternatively plano-convcave. In a preferred embodiment of the four lens design, the four lenses include at least five geometrically and/or optically non-planar surfaces. For example, the negative lens preferably has two such non-planar surfaces.

The objective is preferably corrected over a bandwidth of at least substantially 10 nm. The objective may include a diffractive surface disposed, e.g., on the front surface of the second positive lens, such that the objective may be corrected over a greater bandwidth of substantially 100 nm or more.

Each lens of the objective may comprise a low-dispersion, crown-like material such as COC, Zeonex™ and/or LAK-10. In another embodiment, the first and second positive lenses comprise the low-dispersion, crown-like material, and the third negative lens comprises a higher dispersion, flint-like material such as polystyrene. For the four lens design, the fourth lens may preferably comprise the low-dispersion, crown-like material. One or more of the lenses may be gradient index lenses.

A miniature microscope objective in accordance with the present invention is particularly advantageous in a miniature microscope array (MMA). In such a MMA, multiple objectives are combined into an array of miniature objectives.

Figure 5:
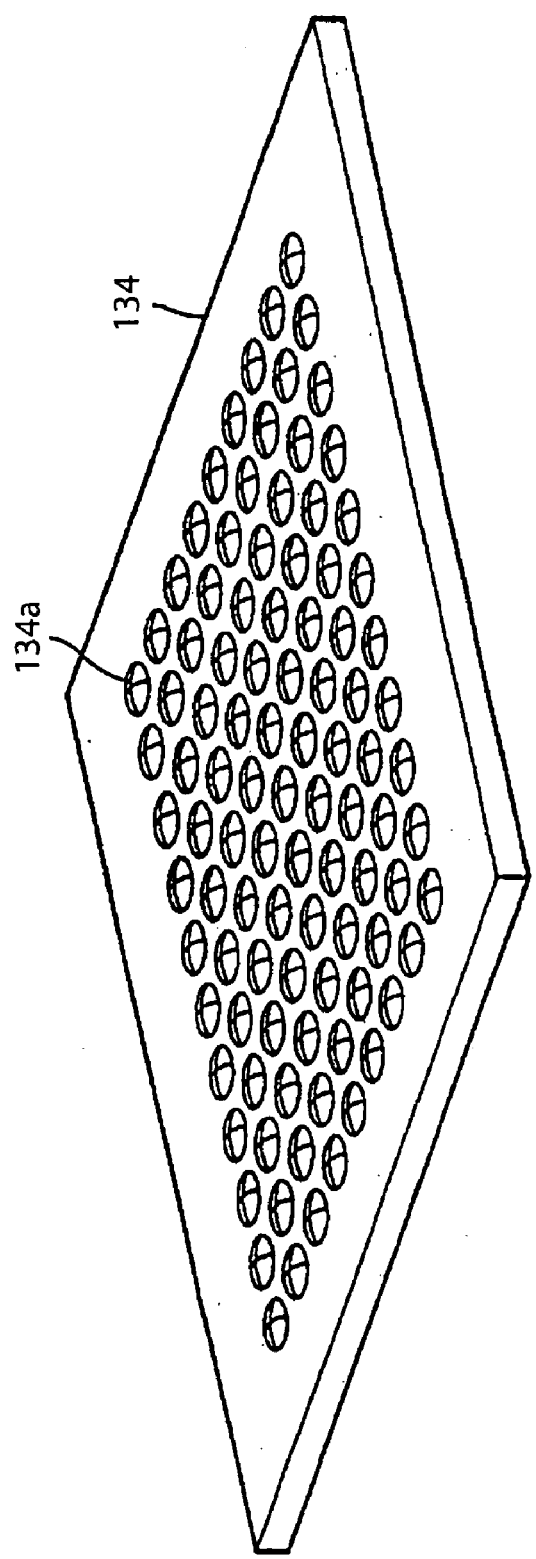
FIG. 5 schematically illustrates a refractive plate patterned with an array of lenslets according to a preferred MMA embodiment.

FIG. 5 schematically illustrates a refractive plate patterned with an array of lenslets according to a MMA embodiment set forth in further detail at PCT/US02/08286, incorporated by reference above. In a preferred embodiment, refractive plates are fabricated as a composite refractive plate 134 as shown in FIG. 5 which includes an array of printed optical elements 134a. The refractive plates can be lithographically printed, embossed, molded, or laser-printed with the optical elements such as for example lenslets, aspherical lenses, diffractive components, cubic phase plates.

Figure 6:
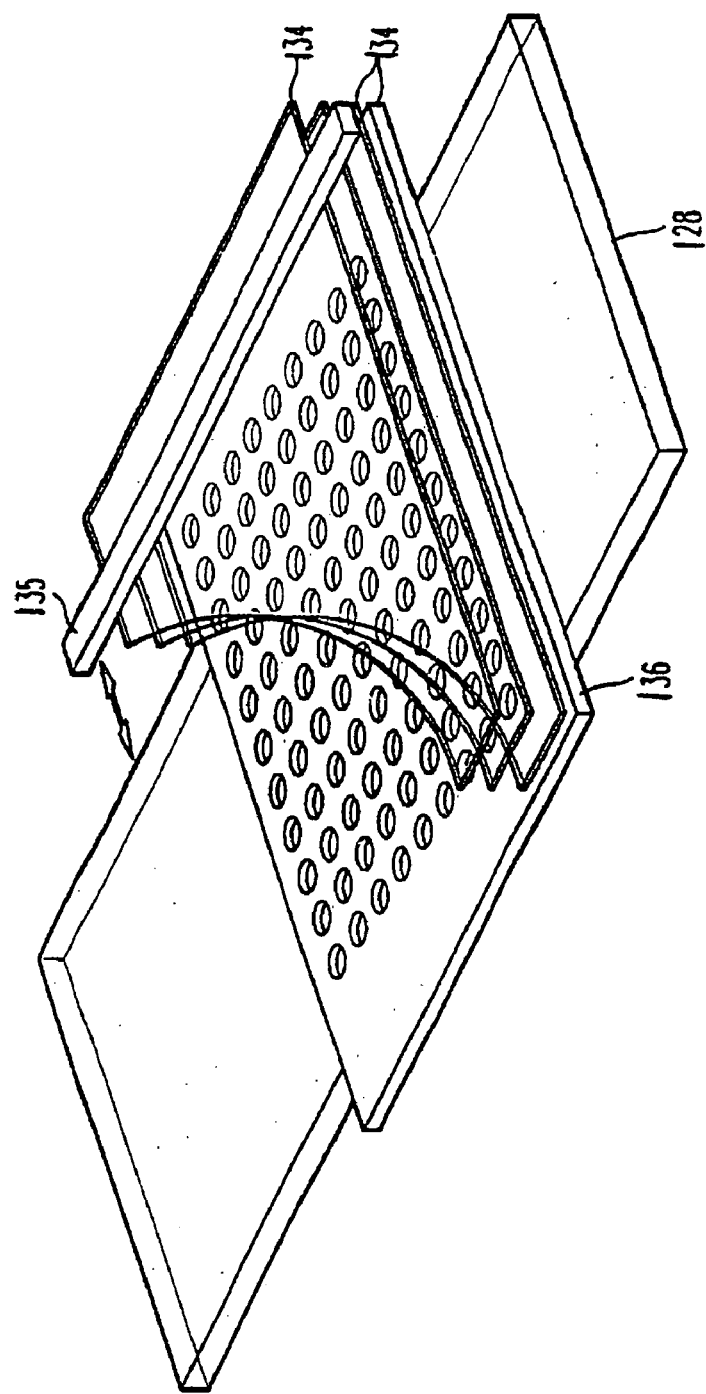
FIG. 6 schematically illustrates a composite base plate and three composite refractive lens plates according to a preferred MMA embodiment.

FIG. 6 schematically illustrates a composite base plate 136 and three composite refractive lens plates 134 according to the MMA embodiment referred to above with reference to FIG. 5. The composite refractive plates 134 are stacked above the composite base plate 136 as shown in FIG. 6. The composite base plate 136 includes an array of embedded optical elements, such as, for example, plano-convex objective lenses, or otherwise as set forth in the exemplary optical prescriptions above, or at the U.S. Ser. No. 10/247,811 application, incorporated by reference above.

The stacked set as shown in FIG. 6 is aligned with the optical elements 135 and the objective lenses directly above each other. Also shown in FIG. 6 as the image sensor is a linear photodetector array located in an image plane of the MA. Scanning of the MA across the sample forms line-by-line images of the object which are concatenated into a composite image of the object. The linear photodetector array 135 can include multiple linear photodetector arrays. The arrangement is shown positioned over a microscope slide 128 that may contain an object to be scanned.

Figure 7:
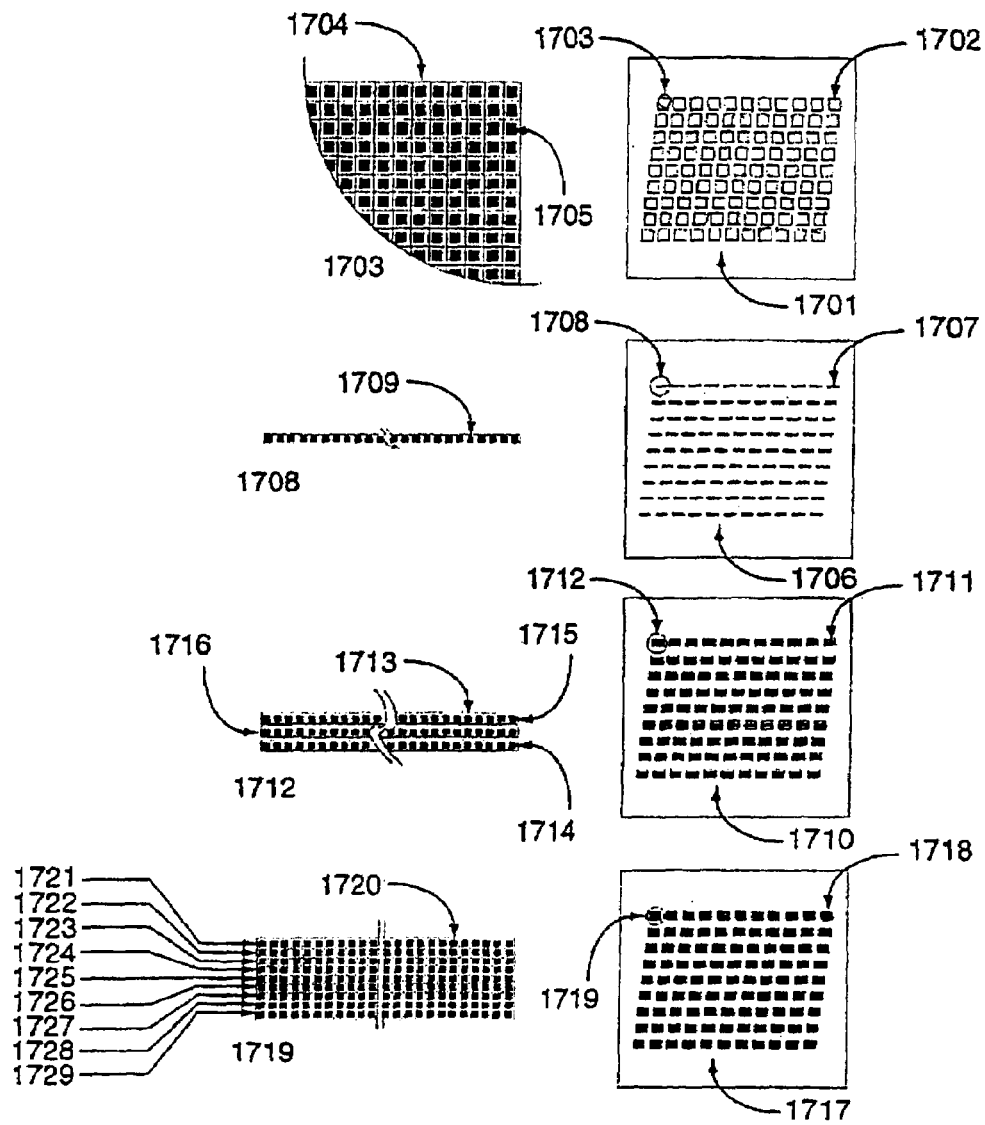
FIG. 7 schematically illustrates image sensor formats according to preferred MMA embodiments.

FIG. 7 schematically illustrates image sensor formats according to further MMA embodiments set forth at the '08286 PCT application. FIG. 7 presents photodetector configurations that can each be used in the image plane of the MA. Image sensor 1701 includes a staggered array of two-dimensional (2D) photodetector arrays 1702. FIG. 7 shows a magnified segment 1703 of a 2D photodetector array 1702. Each 2D photodetector array 1702 includes a rectangular array of pixels 1704. Each pixel 1704 includes a photosensitive region 1705. Alternatively, image sensor 1706 includes a staggered array of one-dimensional (1D) photodetector arrays 1707. FIG. 7 shows a magnified view 1708 of a 1D photodetector array 1707. Each 1D photodetector array 1707 includes pixels. There may be, for example, 512 pixels in each 1D photodetector array 1707. Each pixel contains a photosensitive region 1709. Alternatively, image sensor 1710 includes a staggered array of groups of 1D linear photodetector arrays 1711.

FIG. 7 further shows a magnified view 1712 of a group of 1D linear photodetector arrays 1711. Each 1D photodetector array 1714, 1715, and 1716 includes pixels. Each pixel contains a photosensitive region 1713. In the case of image sensor 1710, the 1D photodetector arrays 1714, 1715, and 1716 may each be covered by a different spectral filter, e.g, 1714 is covered with a filter that transmits red (R) light, 1715 is covered with a filter that transmits green (G) light, and 1716 is covered with a filter that transmits blue (B) light, such that scanning of the MA across the sample forms line-by-line images of the object which are concatenated into a composite color, e.g, R-G-B, image of the object. The center wavelengths of the red filter covering 1714, the green filter 1715, and the blue filter covering 1716 maybe 635 nm, 532 nm, and 430 nm, respectively. Other filter center wavelengths, filter spectral bandwidths, and filter configurations are possible.

The 1D photodetector arrays 1714, 1715, and 1716 may also exhibit different pixel-to-pixel spacing. The choice of the pixel-to-pixel spacing associated with 1714, 1715, and 1716 is dictated by the choice of the spectral filter on each of these ID photodetector arrays and a miniature microscope objective's lateral chromatic aberration (LCA) associated with each filter's center wavelength. By adjusting the pixel-to-pixel spacing associated with 1714, 1715, and 1716, variation with wavelength of transverse magnification may be minimized, reducing the need to process collected image data after the image data are detected by the image sensor. Alternatively, image sensor 1717 includes a staggered array of groups of 1D photodetector arrays 1718.

FIG. 7 further shows a magnified view 1719 of a group of ID photodetector arrays 1718. In this configuration, the image of the object is swept over the group of 1D photodetector arrays 1718 in a direction perpendicular to the photodetector rows 1721, 1722, 1723, 1724, 1725, 1726, 1727, 1728, and 1729. The charge built up at each pixel is moved along each photodetector column at the same rate as the image. This method of reading out signal is known as time-delay-and-integration (TDI) mode. In the case of TDI, the noise variance and the charge grow linearly with the number of rows in the group of 1D photodetector arrays 1718. Consequently, the signal-to-noise (SNR) ratio is improved relative to a single 1D photodetector array by the square root of the number of rows in 1718. The effects of fixed pattern noise are also diminished by averaging over each photodetector column, similar to that described in G. H. Rieke, "Detection of Light: From the Ultraviolet to the Submillimeter", Ch. 7 (Cambridge University Press, 1994; ISBN: 0 521 57674 1) and R. G. Driggers, et al., "Introduction to Infrared and Electro-Optical Systems", Ch. 8 (Artech House, 1999; ISBN 0-89006-470-9), the entire contents of which are incorporated herein by reference.

Image sensor 1701 is well matched to the case in which the MA moves along a longitudinal direction of a glass slide, or vice versa, and stops momentarily and repeatedly to acquire two-dimensional images of portions of the object. Image sensors 1706, 1710, and 1717 are well matched to the case in which the MA moves along a longitudinal direction of a glass slide, or vice versa, without halting and at a constant velocity while the image sensors 1706, 1710, and 1717 record line-by-line images of the object.

In another embodiment, the image sensor 1710 may be configured in a staircase configuration, to permit simultaneous imaging of object features at different depths in the object or at different heights on the object. In this case, an image sensor such as image sensor 1710 may be covered with a mask that includes a plurality of transparent strips ofan optical material.

Those skilled in the art will appreciate that the just-disclosed preferred embodiments are subject to numerous adaptations and modifications without departing from the scope and spirit of the invention. Therefore, it is to be understood that, within the scope and spirit of the invention, the invention may be practiced other than as specifically described above. The invention is therefore not limited by any of the description of the preferred embodiments, and is instead defined by the language of the appended claims, and structural and functional equivalents thereof.

In addition, in the method claims that follow, the steps have been ordered in selected typographical sequences. However, the sequences have been selected and so ordered for typographical convenience and are not intended to imply any particular order for performing the steps, except for any claims wherein a particular ordering of steps is expressly set forth or understood by one of ordinary skill in the art as being necessary.

What is claimed is:

1. A multi-spectral miniature microscope objective imaging system, comprising:
   a multi-spectral imaging miniature microscope objective that is not substantially chromatically corrected for imaging the object at multiple spectral bands at least including a first band and a second band;
   a first detector for detecting a first image corresponding to the first band separated from other wavelengths including the second band; and
   a second detector for detecting a second image corresponding to the second band separated from other wavelengths including the first band, the first and second detectors contemporaneously detecting the first and second images, respectively.

2. A multi-spectral miniature microscope objective imaging system, comprising:
   a multi-spectral imaging miniature microscope objective that is not substantially chromatically corrected for imaging the object at multiple spectral bands at least including a first band and a second band;
   a first detector for detecting a first image corresponding to the first band separated from other wavelengths of the light including the second band; and
   a second detector for detecting a second image corresponding to the second band separated from other wavelengths of the light including the first band, the first and second detectors detecting the first and second images, respectively, in a same image field.

3. The system of claim 2, the first and second images non-overlapping in said same image field.

4. The system of claim 2, the first and second detectors contemporaneously detecting the first and second images, respectively.

5. The imaging system of any of claims 1 or 2, further comprising a processor for combining data from the first detector and the second detector into a multi-spectral image.

6. The imaging system of any of claims 1 or 2, further comprising one or more illuminating light sources for illuminating the object with light at least including the first band and the second band.

7. The imaging system of claim 6, at least one of the one or more illuminating light sources comprising a broadband trans-illuminating light source.

8. The imaging system of claim 6, the one or more illuminating light sources comprising multiple discrete spectral bands of light.

9. The imaging system of claim 6, at least one of the one or more illuminating light sources comprising an epi-illuminating light source.

10. The imaging system of claim 9, further comprising a reflector for reflecting the illuminating light towards the object for reflecting the light from the object to be imaged.

11. The imaging system of claim 9, the one or more illuminating light sources being oriented to transmit the light towards the object for reflecting from the object to be imaged.

12. The imaging system of claim 6, further comprising a reflector for reflecting the illuminating light towards the object for reflecting the light from the object to be imaged.

13. The imaging system of claim 12, the one or more illuminating light sources at least including a first source and a second source generating the first band and the second band, respectively.

14. The imaging system of any of claims 1 or 2, the multiple spectral bands including a third band, the system further comprising a third detector for detecting a third image corresponding to the third band separated from other wavelengths including the first and second bands.

15. The imaging system of claim 14, the first, second and third bands comprising red, blue and green, respectively.

16. The imaging system of any of claims 1 or 2, further comprising a first spectral filter before the first detector for filtering light outside the first band from the first image, and a second spectral filter before the second detector for filtering light outside the second band from the second image.

17. The imaging system of claim 16, the first and second detectors being disposed at a same axial position.

18. The imaging system of claim 16, the first and second bands having different optical path lengths, the system further comprising a block of material in the optical path between the object and the first detector for adjusting the geometrical path length of the first band to be substantially the same as that of the second band.

19. The imaging system of claim 18, the block of material having plane-parallel surfaces with one or more anti-reflections coatings.

20. The imaging system of claim 16, the first and second detectors being disposed at different axial positions corresponding to different axial path lengths.

21. The imaging system of claim 16, further comprising a processor for digitally resealing the first image corresponding to the detected first band to the substantially same size as the second image corresponding to the detected second band, and for combining data corresponding to the digitally rescaled first image and the second image into a multi-spectral image.

22. The imaging system of claim 16, the first detector including multiple pixels of a first pixel size detecting the first image corresponding to the first band and the second detector including multiple pixels of a second pixel size detecting the second image corresponding to the second band, the first and second pixel sizes having a substantially same ratio as sizes of the first and second images, the system further comprising a processor for combining data corresponding to the first and second images into a multi-spectral image.

23. The imaging system of any of claims 1 or 2, further comprising a dichroic optic for separating the first band to be incident at the first detector and the second band to be incident at the second detector.

24. The imaging system of any of claims 1 or 2, further comprising a processor for digitally resealing the first image corresponding to the detected first band to the substantially same size as the second image corresponding to the detected second band, and for combining data corresponding to the digitally rescaled first image and the second image into a multi-spectral image.

25. The imaging system of any of claims 1 or 2, the first detector including multiple pixels of a first pixel size detecting the first image corresponding to the first band and the second detector including multiple pixels of a second pixel size detecting the second image corresponding to the second band, the first and second pixel sizes having a substantially same ratio as sizes of the first and second images, the system further comprising a processor for combining data corresponding to the first and second images into a multi-spectral image.

* * * * *